United States Patent [19]
Caskey

[11] Patent Number: 5,838,422
[45] Date of Patent: *Nov. 17, 1998

[54] OPHTHALMOLOGICAL SELF-TEST UNIT FOR EVALUATING MACULAR DEGENERATION

[76] Inventor: Patrick J. Caskey, 5111 Foothill Ranch Rd., Santa Rosa, Calif. 95404

[*] Notice: The term of this patent shall not extend beyond the expiration date of Pat. No. 5,641,710.

[21] Appl. No.: 771,542

[22] Filed: Dec. 23, 1996

Related U.S. Application Data

[63] Continuation-in-part of Ser. No. 582,610, Jan. 3, 1996, Pat. No. 5,646,710.
[51] Int. Cl.$^6$ ...................... A61B 3/02; A61B 3/00
[52] U.S. Cl. ............... 351/223; 351/200; 351/243
[58] Field of Search ........................ 351/222, 223, 351/224, 237, 243, 200; 40/642; 248/309.4

[56] References Cited

U.S. PATENT DOCUMENTS

| | | | |
|---|---|---|---|
| 3,787,112 | 1/1974 | Lyons | 351/18 |
| 4,063,807 | 12/1977 | Gelius et al. | 351/24 |
| 4,310,978 | 1/1982 | Stern | 40/600 |
| 4,346,968 | 8/1982 | Melin et al. | 351/23 |
| 4,605,292 | 8/1986 | McIntosh | 248/309.4 |
| 5,067,806 | 11/1991 | Kwasman | 351/233 |
| 5,646,710 | 7/1997 | Caskey | 351/223 |

OTHER PUBLICATIONS

*Magnetic Amsler Grid*; "Argus, American Academy of Ophthalmology", Jul. 1997; vol. XVII, No. 7; p. 29.

*Primary Examiner*—Huy Mai
*Attorney, Agent, or Firm*—Fish & Richardson P.C.

[57] ABSTRACT

An improved ophthalmological self test unit for assisting in the self evaluation of the degenerative effects of certain eye disorders. The self diagnostic ophthalmological device includes a first layer having a top rewriteable surface and a grid pattern disposed thereon and a magnetic second layer fixedly attached to the first layer for attaching the self test device to a magnetically permeable surface.

24 Claims, 7 Drawing Sheets

PRIOR ART

OPHTHALMOLOGICAL SELF-TEST UNIT FOR EVALUATING MACULAR DEGENERATION

This is a continuation-in-part of U.S. application Ser. No. 08/582,610, entitled "OPHTHALMOLOGICAL SELF-TEST UNIT FOR EVALUATING MACULAR DEGENERATION", filed on Jan. 3, 1996, now U.S. Pat. No. 5,646,710.

BACKGROUND

The present invention relates generally to ophthalmological diagnostic equipment and particularly to an ophthalmological self-test unit which combines features of a standard Amsler grid with an attention focusing device in a convenient package for use in assisting a patient to consistently evaluate macular degeneration over time.

Macular degeneration is a retinal disease which is the leading cause of central vision loss among people over the age of 65. Macular degeneration is a process of wear and tear in the macula, the portion of the retina responsible for sharp central vision and color perception. It usually affects both eyes, causing vision loss which may be either gradual or abrupt.

Referring to FIG. 1, a cross sectional view of a human eye is shown. The human eye is designed for panoramic viewing, allowing an individual to see objects straight ahead as well as to the side. As light enters the eye 10, it passes through the cornea 11 and pupil 12, and is focused by lens 13 into an image on retina 14. This image is converted by the retina into electrical impulses which are transmitted via optic nerve 15 to the brain. Macula 16 is the particular portion of the retina at which sharp central vision is processed.

The macula consists of multiple layers as is shown in FIG. 2. Innermost layer 18 of macula 16 is comprised of light sensing cells which produce sharp central vision. Two underlying layers nourish and help remove waste materials from these light sensing cells. The light sensing cells or "cones" as they are commonly referred to, are responsible for color perception and central vision. These cones shed their outer segments as waste products through normal metabolism. Second layer 20, known as the "retinal pigment epithelium", nourishes the cones and digests these shed outer segments during the day. Finally, third layer 22, known as the "choroid", comprises blood vessels that transport nutrients and carry away waste material from the macula region.

Macular degeneration is the common name for the age-related disease where macular retinal pigment epithelium cells function less well than normal. As a result, waste removal and nutrition of the cones suffers, causing central vision loss. Macular degeneration can be further classified into two varieties: a "dry type" and a "wet type". Dry type macular degeneration occurs when the outer segments of the light sensing cones, which are continuously being shed, are unable to be digested by the pigment epithelium layer of the macula. Consequently the pigment epithelium layer swells and eventually dies after accumulating too much undigested material from the cones. Yellowish deposits of this waste material gradually develop under the retina between the choroid and pigment epithelium. In this "dry type" macular degeneration, the vision loss is characterized by gradual blurring or partial obscuration of central vision as a result of parts of the macula having begun to die, creating areas where the cones are no longer functional. Clinically, the person suffering from this type of the disease may experience relatively mild central visual distortion with straight lines appearing bent or wavy.

In the second or "wet" type of this disorder, more severe and sudden vision loss may occur. This sort occurs when abnormal new blood vessels or "neovascular membranes" grow from the choroid through the damaged pigment epithelium and under the macula. These neovascular membranes are fragile and are prone to hemorrhage which results in severe distortion of the macular tissue. As a result, the light sensing cells (cones) become separated from their source of nutrients and suffer further damage due to scarring as the hemorrhage occurs over time. With this type of disorder, dark or "missing" spots in the central vision may occur rapidly and with little warning due to these hemorrhagic changes. Fortunately, intervention with laser therapy early in this process may prevent additional vision loss.

In order to detect changes early enough such that laser therapy is beneficial, doctors use a variety of tests designed to evaluate the health of the macula. One such test uses an "Amsler grid". An Amsler grid includes a uniform grid pattern of crossing lines. The use of this grid reveals distortions and other abnormalities in the central field of vision. A patient once having been diagnosed with macular degeneration is typically required to monitor their vision with an Amsler grid on a daily basis in order to detect subtle signs of increasing distortion which may indicate an evolving neovascular membrane. Since the "wet" form of the disease may occur suddenly and with rapid vision loss, daily follow up is essential to ensure that intervention with laser treatment is instituted early enough to help prevent further visual damage.

The Amsler grid is known in the art (See FIG. 3). The use of the Amsler grid requires that a patient stand about a foot away from the grid itself, and, while wearing one's own glasses, cover or close one eye and focus on the center of the grid. In order for the Amsler grid to be effective, the patient must note any changes that occur over time and repeat the above process on a daily basis. While Amsler grids have been known for years, the use of the grid in a practical setting by patients has revealed a number of every day problems.

Because of the nature of this degenerative eye disorder, daily use is required in order to track changes associated with the disorder such that early effective treatment can be implemented. As such, the grid must be accessible and easy to use in order to encourage use of the product. Secondly, the grid must also be sufficiently sized to accommodate the self testing of both the user's central and peripheral vision. A grid which is too small won't allow for the evaluation of a sufficient field of vision, yielding inaccurate or incomplete test results. However, the grid must not be so large as to become a nuisance to manipulate or store.

The degenerative nature of the eye disorder also requires that a patient be able to monitor the progress of the disease by somehow recording the particular areas of concern associated with each of the patient's eyes for a given baseline time frame, in order to determine whether or not any further damage has arisen.

As described previously, the basic architecture of the Amsler grid includes a grid area which is utilized by the patient to assist in the evaluation of their vision. In practice patients have suggested that because of the poor contrast of the fixation target on the grid, they often find themselves, and their eye that they are testing, wandering after but a few brief seconds when using the grid.

SUMMARY OF THE INVENTION

In general in one aspect, the invention provides an ophthalmological self test apparatus for assisting in the daily evaluation of the human eye including a first layer having a top rewriteable surface and a grid pattern disposed thereon and a magnetic second layer fixedly attached to the first layer for attaching the invention to a magnetically permeable surface.

Preferred embodiments include the following features. The grid is polar including concentric circles and radial lines.

In another aspect, the invention provides an ophthalmological self test apparatus including a first layer having a top and bottom surface and a centrally disposed aperture therebetween. The top surface has a grid pattern disposed thereon. The apparatus includes focusing means includes a light source disposed in the aperture for allowing light to be emitted from the aperture at the top surface and a switch coupled to the light source for activating the light source.

Preferred embodiments of the invention include the following features. The focusing means further includes a focusing pattern disposed on the top surface of the top layer and over the grid pattern. The focusing pattern including a plurality of lines extending from a periphery of the top surface toward the centrally disposed aperture. The focusing pattern may be a different color than the grid pattern and may include a pair of diagonal lines or a target cross hair pattern. The bottom surface is constructed from a static adhesive material allowing for static adhesion to a surface or a magnetic material allowing for adhesion to a magnetically permeable surface. The static adhesive material is vinyl.

In another aspect, the invention provides an ophthalmological self test apparatus including a first layer having a top and bottom surface and a centrally disposed aperture therebetween. The top layer has a grid pattern disposed thereon. The apparatus includes focusing means including a light source disposed in the aperture for allowing light to be emitted from the aperture at the top surface, switching means coupled to the light source for activating the light source and an attachment layer for attaching the self test apparatus temporarily to a surface allowing for removal and replacement of the self test apparatus from the surface.

In another aspect, the present invention provides an ophthalmological self test apparatus including a first layer having a top surface having a grid pattern disposed thereon, a light source centrally disposed on the top surface at a center of the grid pattern, a switch coupled to the light source for activating the light source and a magnetic second layer fixedly attached to the first layer for maintaining the self test apparatus upon attachment to a magnetically permeable surface.

In another aspect, the invention provides an ophthalmological self test apparatus including a first layer having a top rewriteable and a bottom surface and a centrally disposed aperture therebetween. The top surface having a grid pattern disposed thereon. The invention including a light source disposed in the aperture for allowing light to be emitted from the aperture at the top surface, and a switch coupled to the light source for activating the light source.

In another aspect, the invention provides an ophthalmological self test apparatus including a first layer having a top and bottom surface and a centrally disposed aperture therebetween. The top surface having a grid pattern disposed thereon. The invention includes a light source disposed in the aperture for allowing light to be emitted from the aperture at the top surface, a switch coupled to the light source for activating the light source and an attachment layer fixedly attached to the first layer for attaching the self test apparatus temporarily to a surface.

In another aspect, the invention provides an ophthalmological self test apparatus including a first layer having a top rewriteable surface and a bottom surface and a centrally disposed aperture therebetween. The top surface having a grid pattern disposed thereon. The invention including a reflector disposed in the aperture for allowing light to be reflected from the aperture at the top surface.

In another aspect, the invention provides an ophthalmological self test apparatus including a first layer having a top rewriteable surface and a grid pattern disposed thereon and a reflector centrally disposed on the top surface for allowing light to be reflected toward a human eye.

One advantage of the present invention is a baseline configuration is easily stored and maintained thereby allowing for easy monitoring for subsequent changes in a patient's vision.

Another advantage of the present invention is that it provides a convenient packaging for ease of storage in locations throughout a patient's household to encourage daily testing.

Another advantage of the present invention is that it maintains a patient's attention focused squarely on the grid so as to allow for a more accurate evaluation of the patient's vision.

Another advantage of the present invention is that the device allows for the easy location of the grid in well traveled portions of the patient's residence.

Other advantages and features will be apparent from the following description and claims.

BRIEF DESCRIPTION OF THE DRAWINGS

Initial objects and features of the invention will be more readily apparent from the following detailed description and appended claims when taken in conjunction with the drawings, in which:

DETAILED DESCRIPTION 5

Figure 1:
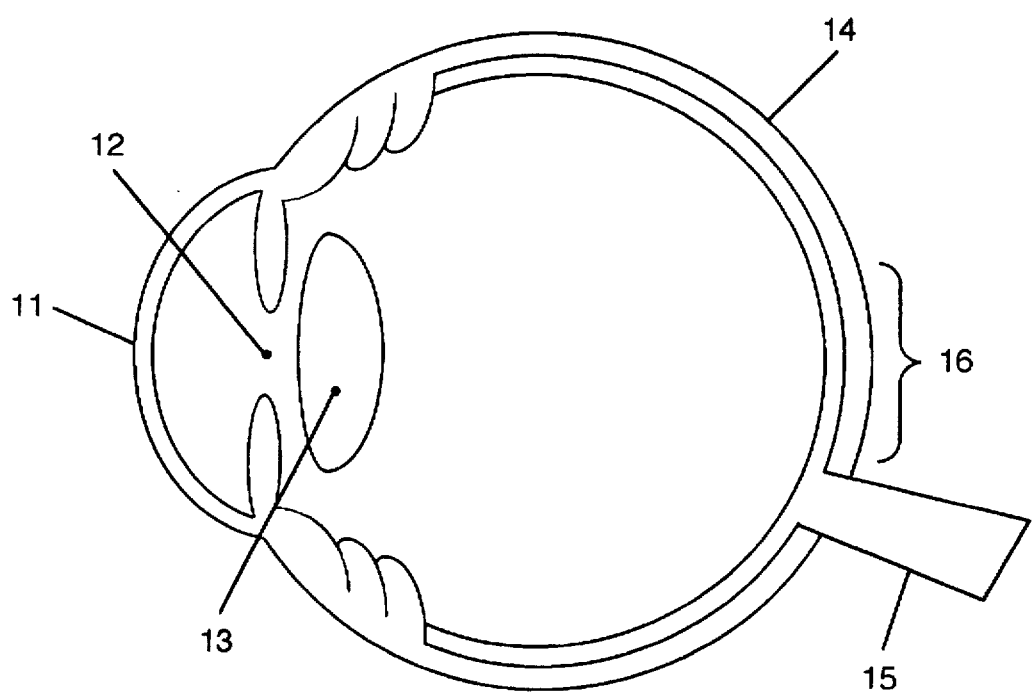
FIG. 1 is a cross section diagram a human eye.
Figure 2:
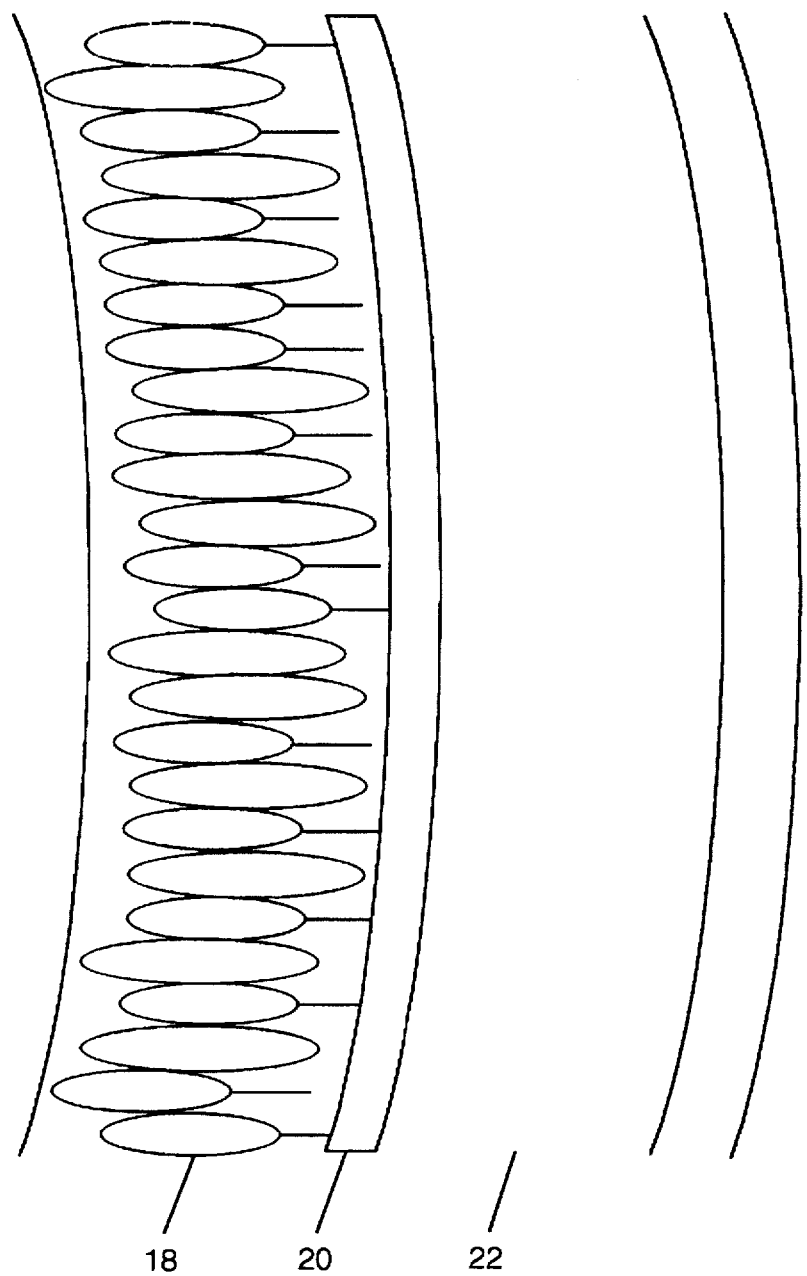
FIG. 2 is a cross section of a macular portion of the human eye.
Figure 3:
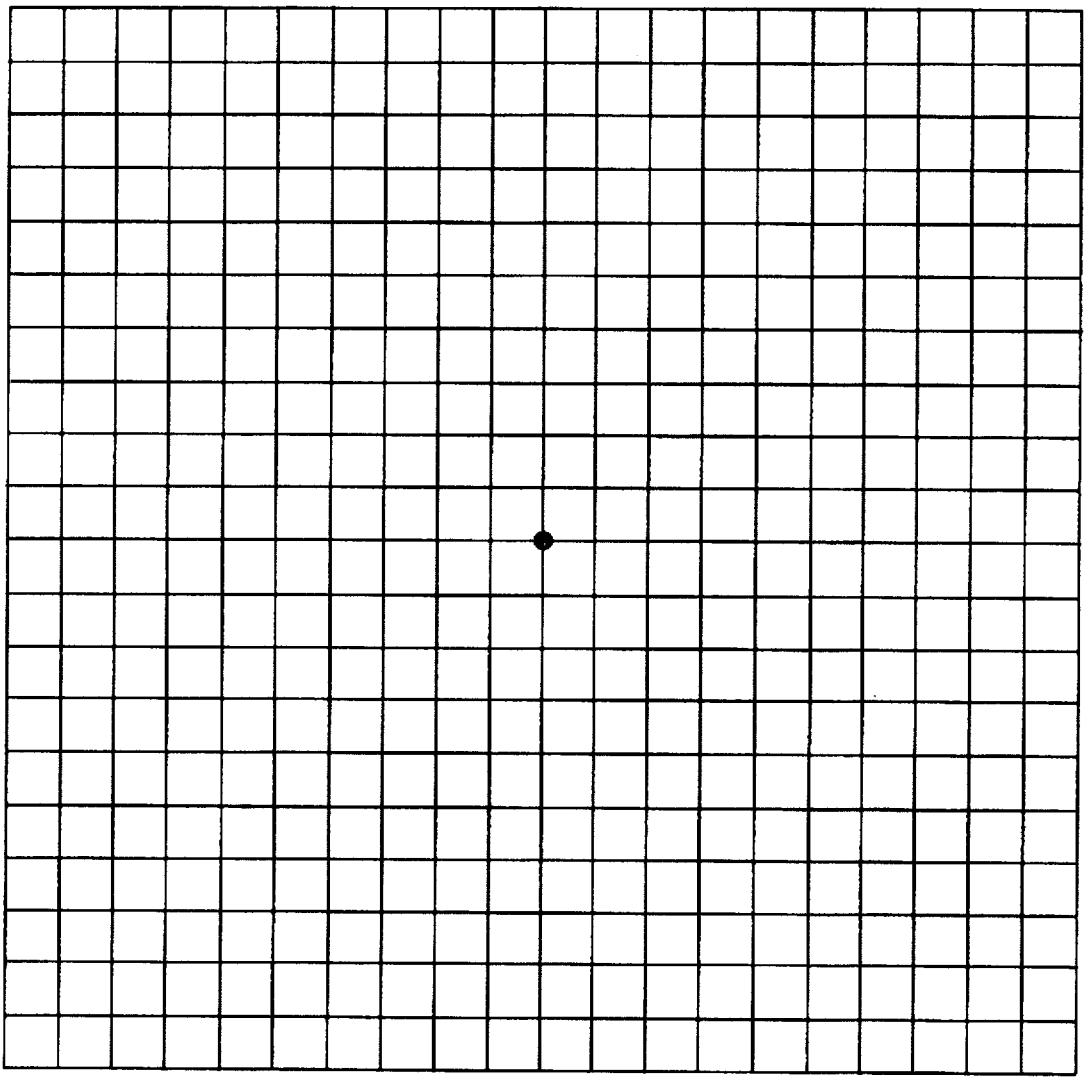
FIG. 3 is a prior art Amsler grid.
Figure 4:
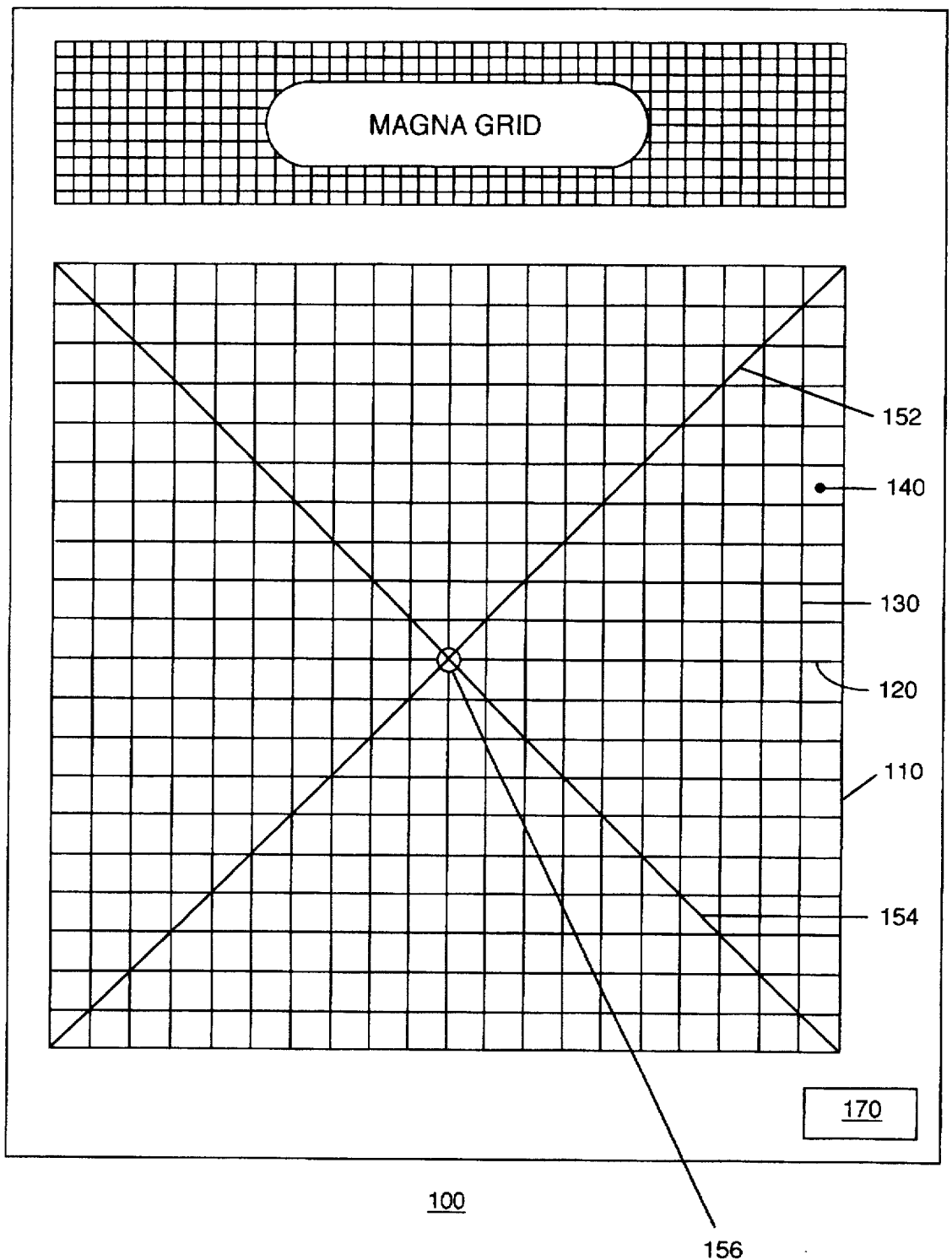
FIG. 4 is a grid structure according to one embodiment of the present invention.

Referring to FIG. 4, there is shown a diagram of a grid 100 according to one embodiment of the present invention. In this embodiment, the grid 100 is comprised of a grid area 110 which includes twenty horizontal lines 120 and twenty vertical lines 130. The horizontal and vertical lines are spaced to form one hundred individual boxes 140 in an overall grid size of 5"×5". Those ordinarily skilled in the art will recognize that as the grid size is made smaller, less area of the peripheral vision associated with a particular patient may be mapped by the diagnostic tool. Accordingly, a minimum grid size of approximately four inches square (4×4) should be utilized in order to effectively cover the region associated with the macula. Similarly, those ordinarily skilled in the art will recognize that grids much bigger than represented will offer little or no help in diagnosing the progress of the disease because of the centrally located distortion effects associated with this particular eye disorder. Accordingly, a maximum grid size of approximately eight inches square (8×8) should be utilized. A grid size of five inches by five inches is preferred.

The spacing of the vertical/horizontal lines is done to accommodate the recognition by the patient of discrepancies from a norm. As the grid lines are drawn tighter and tighter together, the "busyness" of the grid tends to mask certain manifestations of the disorder. Accordingly, a grid square resolution on the order of between 0.05 and 0.09 square inches is recommended, with a grid size of 0.0625 square inches used in one embodiment. Disposed on grid area 110 is focusing means 150. In one embodiment, focusing means 150 is comprised of a focusing pattern including a pair of red diagonal lines 152 and 154 which extend from the respective corners formed by grid horizontal and vertical lines 120 and 130 through the center of grid area 110. Alternatively, the focusing pattern may be a target cross hair as would be commonly found in a gun sight. In one embodiment, the color of the focusing means is different from the grid pattern to assist in the focusing operation.

At the center of focusing means 150 is light source 156. In one embodiment, light source 156 is a light emitting diode (LED). In use, patients have reported that the centrally located light source coupled with red diagonal focusing lines serve to center the patient's attention fixedly on the central portion of the grid thereby allowing for repeatable test results. Alternatively, light source 156 may be a light bulb, a mirror, a rhinestone, reflector or other sufficiently light emitting or reflecting object as is known in the art. Light source 156 must be sized sufficiently small to avoid masking any centrally located vision distortion or defects. Accordingly, the light source should be sized to be less than 0.50 inches, and in one embodiment, the light source is an LED which is 3 mm (approximately 0.1 inches) in diameter.

Figure 5:
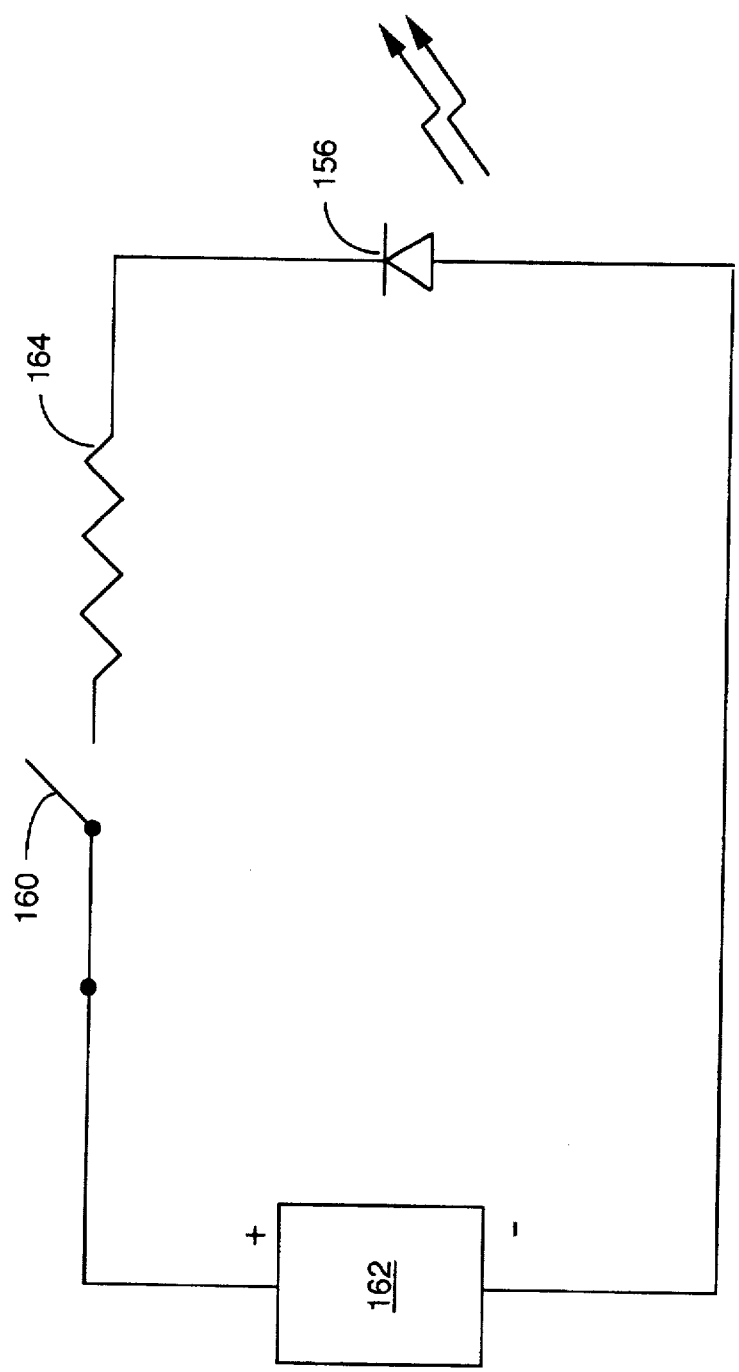
FIG. 5 is a block diagram of a circuit associated with the focusing means of one embodiment of the present invention.

Referring to FIG. 5, a circuit diagram associated with the electrical portion of focusing means 150 is shown. Light source 156 is attached at one end to a resistor 164 whose other end is coupled to the normally open contact of switch/relay 160. The common contact of the switch /relay 160 is in turn attached to the positive lead of power source 162. Finally, the second lead from light source 156 is coupled to the negative lead of power source 162 forming a complete circuit. In the one embodiment, switch 160 is a single pole single throw manual switch, power source 162 is a lithium battery part number BR-2/3AA manufactured by Panasonic, resistor 164 is a 500 ohm resistor, and light source 156 is a light emitting diode part number BL-B5131-L manufactured by American Bright Optoelectronics Co. Those ordinarily skilled in the art will recognize that the parts were selected to minimize the overall profile of the components, while providing a sufficiently long life and duty cycle upon energization of light source 156 to allow a user to perform a complete test. As such, other similar parts may be substituted as is known in the art without departing from the true spirit of the present invention. Alternatively, switch relay 160 may be a Bipolar or Field Effect transistor, or an SCR, or any other electronic switch as is known in the art. Power Source 162 may alternatively be a solar cell, or other power source as is known in the art.

In operation, upon depressing manual switch/relay 160, power source 162 provides a voltage source at the positive lead to light source 156. Resistor 164 current limits the power source 162 providing for a sufficient amount of current to drive the LED, while minimizing the drain on the power source 162. Light source 156 will illuminate for as long as the manual switch is actuated, allowing for the user to easily focus on the center of the grid portion. Upon deactivating the manual switch/relay 160, the light source is no longer powered, thereby conserving the battery power.

In an alternative embodiment, light source 156 is configured to operate intermittently (flash) over the period of activation. This is accomplished, for example, by providing a flasher control circuit (not shown) between power source 162 and light source 156. In one embodiment, the flasher control circuit may be implemented by the use of capacitors to cause a simple saw tooth waveform to be delivered to the light source thereby resulting in the flashing action. Alternatively, a timer circuit employing, for example, a "555" timer is implemented between manual switch 164 and light source 156 to effectuate the flashing. Alternatively, a flashing LED may be utilized which incorporates the control circuit into the LED package. Flashing LEDs are available from the American Bright Optoelectronics Co.

In one embodiment, power source 162, resistor 164, and relay 160 are packaged within a single block 170 as shown in FIG. 4. Block 170 is attached to the surface of grid 100 and allows for the easy removal and replacement of battery 162. In one embodiment, block 170 is comprised of molded plastic. Block 170 is fashioned to extend a minimal height above the surface of grid area 110 to minimize the occurrence of knocks or bumps to the device.

Figure 6:
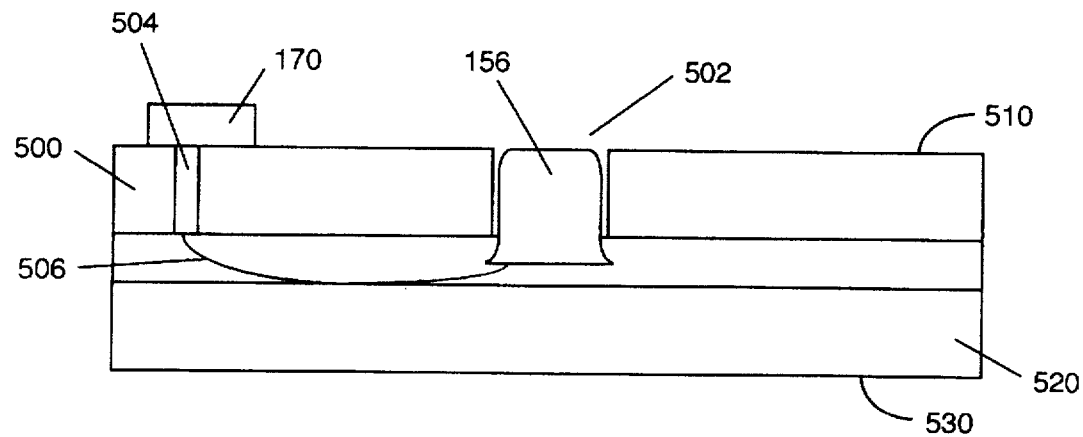
FIG. 6 is a cross section of the grid structure of FIG. 4.

Referring to FIG. 6, a cut away view of grid 100 is shown. In one embodiment, grid 100 is comprised of a top layer 500 having a first recess 502 for receiving light source 156 and aperture 504 for allowing interconnecting wires 506 to pass through top layer 500 for connection to power source 162 mounted in block 170. Top layer 500 includes an upper surface 510 which is made from a high contrast, low gloss, erasable, re-writable material which allows for the easy writing and recording of baseline information on the grid surface. The re-writable surface also allows for ease of erasing or correcting any mistakes made in the course of the diagnostic process. In use, this ease of correction feature has helped to encourage patients to map out affected portions of their vision which are abnormal, while non-erasable surfaces have been found to frustrate and even discourage patients from marking on the grid. As was disclosed above, ease of use coupled with patient comfort in recording baseline information have been found to be the keys to continued use of the test aid, and necessarily the early detection of degradations in the patient's vision. In one embodiment, upper surface 510 is comprised of vinyl. However, other materials which allow for ease of writing and erasing may be substituted as is known in the art.

Top layer 500 is disposed over a bottom layer 520 enclosing interconnecting wires 506 between the two layers. Bottom layer 520 includes a bottom surface 530 comprised of a magnetic material. The top layer is affixed to the bottom layer by any suitable glue material, such as an epoxy resin. In one embodiment, bottom layer 520 is a magnetic backed material composite part number 130 produced by Dowling Miner Magnetics Corporation. The magnetic back material allows for the attachment of the grid to any magnetically permeable (metallic) surface, such as on a refrigerator, or other surface which is located in a portion of the patient's house which is accessed daily. In addition, the magnetic back material allows the patient to quickly and easily store and locate the grid, while the re-writable/erasable surface allows for the preservation of the vital baseline information.

In use, this type of easily accessible, conveniently storable and erasable configuration has been shown to encourage the patient to perform the self-diagnostic test on a daily basis.

In another embodiment, bottom layer 520 is a static adhesion layer constructed from a static adhesion material. The static adhesion material allows for the temporary attachment of the grid to smooth surfaces due to the static cling effects associated with the static adhesion material. Accordingly, temporary attachment of the device may be accomplished to any smooth surface, such as on a mirror or a glass surface. This facilitates the temporary attachment of the device in numerous portions of a patient's house. For example, the device including static adhesion layer may be easily and non-permanently attached to a mirror in a bathroom used by the patient. In addition, the apparatus may be easily relocated while away from home (on travel) again using the static adhesion effect to temporarily attach the apparatus to a smooth surface (such as the bathroom mirror in a hotel room). In one embodiment, bottom layer 520 is a 7.5 mm thick layer of electrostatic vinyl part number 66-VSW-white produced by General Foundations, Inc., Santa Rosa, Calif.

In another embodiment, bottom layer 520 may include a non-permanent adhesive on its bottom surface to allow for the placement, removal and replacement of the device on numerous surface types. A tacky micro sphere adhesive such is used on Post-It™ notes manufactured by 3M may be used.

In another embodiment, light source 156 may be disposed on the surface of the top layer 500. In this configuration, only a single layer structure is required. The single layer structure includes an erasable, rewriteable surface having a grid disposed on a top surface and may be constructed from a static adhesion material. In one embodiment, a single vinyl layer having a thickness between 5 mm and 20 mm which includes a high contrast and low gloss surface is preferred.

Figure 7:
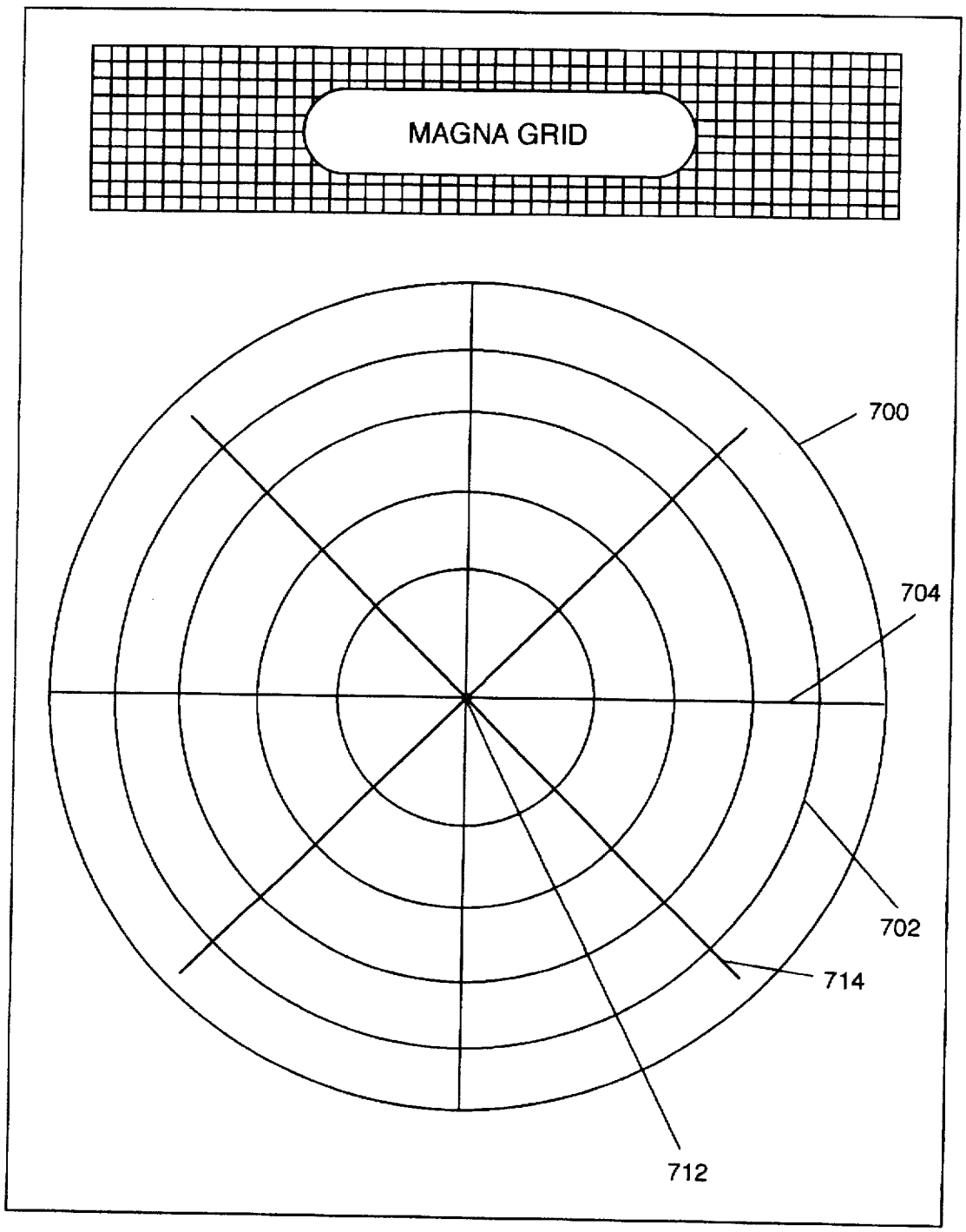
FIG. 7 is an alternative grid structure according to a second embodiment of the present invention.

Referring to FIG. 7, a second embodiment of the grid is shown. In this alternative embodiment, grid area 700 is comprised of a series of concentric circles 702 and radial lines 704. A focusing means 710 including light source 712 and diagonal centering lines 714 are include in this embodiment, and are similar to the focusing means disclosed above. In this embodiment, the attention centering function of focusing means 710 is augmented by the polar grid configuration due to the tunnel affect created by the concentric circles.

In operation, a patient will define a baseline characterization of his vision at his or her respective physicians's office in order to track the progress of this degenerative eye disorder. The baseline characterization is performed by marking on the re-writable/erasable surface of the grid the areas of distortion which have arisen in the particular person's vision as of a baseline time. Thereafter this baseline information may be readily compared to the present results so that the progress of the disease may be monitored.

In use, the grid is to be mounted to a metallic surface, such as found on a common refrigerator door, or to a smooth surface, such as a bathroom mirror, in a well traveled location of the patient's home. The magnetic back mounting (or static adhesion layer) also minimizes the risk of misplacing the grid thereby losing the baseline information that has been developed and recorded on the grid device. The grid being adaptable for easy, convenient, and highly visible storage while not in use, will encourage the patient to repeat the test as necessary and to record all relevant information for discourse with a physician at the appropriate juncture. At the designated hour of a day, the patient can quickly and easily locate the grid, and activate the light source to focus the patient's attention. The focusing means is activated by depressing the manual switch located on the casing. Thereafter, the patient may quickly and easily perform a test on each eye, comparing his or her current vision (and associated defects) against the baseline information stored on the grid. In the event any differences are detected over the baseline, the patient may document these new changes by marking on the grid the areas that have become affected and contact his or her respective physician.

The present invention has been described with reference to a few specific embodiments. The description is illustrative of the invention is not to be construed as limiting the invention. Various modifications may occur to those skilled in the art without departing from the true spirit and scope of the invention as defined by the pending claims.

What is claimed is:

1. An ophthalmological self test apparatus for assisting in the daily evaluation of the human eye, the apparatus comprising:

a first layer having a top rewriteable surface and a grid pattern disposed thereon; and a magnetic second layer fixedly attached to said first layer for attaching said self test apparatus to a magnetically permeable surface.

2. The self test apparatus of claim 1 wherein said grid is polar including concentric circles and radial lines.

3. An ophthalmological self test apparatus for assisting in the daily evaluation of the human eye, the apparatus comprising:

a first layer, said first layer having a top and bottom surface and a centrally disposed aperture therebetween, said top surface having a grid pattern disposed thereon; and focusing means including a light source disposed in said aperture for allowing light to be emitted from said aperture at said top surface.

4. The self test apparatus of claim 3 wherein focusing means further includes a focusing pattern disposed on said top surface of said first layer and over said grid pattern, said focusing pattern including a plurality of lines extending from a periphery of said top surface toward said centrally disposed aperture.

5. The self test apparatus of claim 4 wherein the focusing pattern has a different color than the grid pattern.

6. The self test apparatus of claim 4 wherein said focusing pattern is a pair of diagonal lines.

7. The self test apparatus of claim 4 wherein said focusing pattern is a target cross hair pattern.

8. The apparatus of claim 3 where the bottom surface is constructed from a static adhesion material allowing for static adhesion to a surface.

9. The apparatus of claim 8 where the static adhesion material is vinyl.

10. The apparatus of claim 3 where the bottom surface is constructed from a magnetic material allowing for adhesion to a magnetically permeable surface.

11. The apparatus of claim 3 where the bottom surface includes a tacky micro sphere adhesive for non-permanently attaching the apparatus to an attachment surface.

12. An ophthalmological self test apparatus for assisting in the daily evaluation of the human eye, the apparatus comprising:

a first layer, said first layer having a top and bottom surface and a centrally disposed aperture therebetween, said top surface having a grid pattern disposed thereon;

focusing means, said focusing means including a light source disposed in said aperture for allowing light to be emitted from said aperture at said top surface, and switching means coupled to said light source for activating said light source; and an attachment layer for attaching said self test apparatus temporarily to a surface and allowing for removal and replacement of the self test apparatus from the surface.

13. The apparatus of claim 12 wherein the attachment layer is selected from the group of a magnetic layer, a static adhesion layer and a tacky micro adhesive layer.

14. An ophthalmological self test apparatus for assisting in the daily evaluation of the human eye, the apparatus comprising:

a first layer having a top surface having a grid pattern disposed thereon;

a light source centrally disposed on said top surface at a center of said grid pattern, and a switch coupled to said light source for activating said light source; and a magnetic second layer fixedly attached to said first layer for maintaining said self test apparatus upon attachment to a magnetically permeable surface.

15. An ophthalmological self test apparatus for assisting in the daily evaluation of the human eye, the apparatus comprising:

a first layer, said first layer having a top rewriteable and a bottom surface and a centrally disposed aperture therebetween, said top surface having a grid pattern disposed thereon; and a light source disposed in said aperture for allowing light to be emitted from said aperture at said top surface.

16. An ophthalmological self test apparatus for assisting in the daily evaluation of the human eye, the apparatus comprising:

a first layer, said first layer having a top and bottom surface and a centrally disposed aperture therebetween, said top surface having a grid pattern disposed thereon;

a light source disposed in said aperture for allowing light to be emitted from said aperture at said top surface, and a switch coupled to said light source for activating said light source; and an attachment layer fixedly attached to the first layer for attaching said self test apparatus temporarily to a surface.

17. The apparatus of claim 16 wherein the attachment layer is selected from the group of a magnet layer, a static adhesion layer and a tacky micro adhesive layer.

18. The apparatus of claim 16 further including a flashing circuit coupled between said light source and said switch for operating said light source intermittently.

19. An ophthalmological self test apparatus for assisting in the daily evaluation of the human eye, the apparatus comprising:

a first layer, said first layer having a top rewriteable surface and a bottom surface and a centrally disposed aperture therebetween, said top surface having a grid pattern disposed thereon; and a reflector disposed in said aperture for allowing light to be reflected from said aperture at said top rewriteable surface.

20. The apparatus of claim 19 further including an attachment layer fixedly attached to the first layer for attaching said self test apparatus temporarily to a surface.

21. The apparatus of claim 20 wherein the attachment layer is selected from the group of a magnet layer, a static adhesion layer and a tacky micro adhesive layer.

22. An ophthalmological self test apparatus for assisting in the daily evaluation of the human eye, the apparatus comprising:

a first layer including a top rewriteable surface having a grid pattern disposed thereon; and a reflector centrally disposed on said top rewriteable surface for allowing light to be reflected toward a human eye.

23. The apparatus of claim 22 further including an attachment layer fixedly attached to the first layer for attaching said self test apparatus temporarily to a surface.

24. The apparatus of claim 23 wherein the attachment layer is selected from the group of a magnet layer, a static adhesion layer and a tacky micro sphere adhesive layer.

* * * * *